(12) United States Patent
Lim et al.

(10) Patent No.: US 12,310,788 B1
(45) Date of Patent: May 27, 2025

(54) SYSTEM FOR MEASURING INTRAOCULAR PRESSURE

(71) Applicants: Seongjin Lim, Birmingham, AL (US); Kwanghyun Shin, Seoul (KR); Dongwook Lee, Boston, MA (US)

(72) Inventors: Seongjin Lim, Birmingham, AL (US); Kwanghyun Shin, Seoul (KR); Dongwook Lee, Boston, MA (US); Danin Jeon, Tokyo (JP); Seongjin Park, Seoul (KR)

(73) Assignees: Seongjin Lim, Birmingham, AL (US); Kwanghyun Shin, Seoul (KR); Dongwook Lee, Boston, MA (US)

( * ) Notice: Subject to any disclaimer, the term of this patent is extended or adjusted under 35 U.S.C. 154(b) by 0 days.

(21) Appl. No.: 19/031,849

(22) Filed: Jan. 18, 2025

(30) Foreign Application Priority Data

May 7, 2024 (KR) .................. 10-2024-0059835

(51) Int. Cl.
*A61B 8/10* (2006.01)
*A61B 3/16* (2006.01)
*A61B 8/00* (2006.01)

(52) U.S. Cl.
CPC .............. *A61B 8/10* (2013.01); *A61B 3/16* (2013.01); *A61B 8/485* (2013.01)

(58) Field of Classification Search
CPC .. A61B 8/10; A61B 8/485; A61B 3/16; A61B 3/165
See application file for complete search history.

(56) References Cited

U.S. PATENT DOCUMENTS

| | | |
|---|---|---|
| 2013/0144170 A1 | 6/2013 | Chang et al. |
| 2013/0342810 A1 | 12/2013 | Nishiwaki |
| 2016/0089113 A1 | 3/2016 | Choi et al. |
| 2016/0278741 A1 | 9/2016 | Yang et al. |
| 2019/0125300 A1 | 5/2019 | Kong et al. |

(Continued)

FOREIGN PATENT DOCUMENTS

| | | |
|---|---|---|
| JP | 2013-248312 A | 12/2013 |
| KR | 10-2012-0004687 A | 1/2012 |

(Continued)

OTHER PUBLICATIONS

Ahmed, Hassan M., Nancy M. Salem, and Walid Al-Atabany. "Finite element modelling of corneal biomechanics assessment using ultrasonic elastography." (2022).*

*Primary Examiner* — Carolyn A Pehlke
(74) *Attorney, Agent, or Firm* — Bridgeway IP Law Group, PLLC; Hyun Woo Shin (57) ABSTRACT

An intraocular pressure measurement system includes an ultrasound transmitter configured to generate a first driving signal and a second driving signal, a probe comprising a plurality of transducers, the probe configured to generate a first ultrasound signal based on the first driving signal, generate a second ultrasound signal based on the second driving signal, and irradiate the first ultrasound signal and the second ultrasound signal onto an eyeball, an ultrasound receiver configured to receive an echo signal, which is the reflected second ultrasound signal, through the probe, and generate an ultrasound data based on the echo signal; and an image processing device configured to measure an intraocular pressure of an internal structure of the eyeball.

4 Claims, 4 Drawing Sheets

(56) References Cited

U.S. PATENT DOCUMENTS

2020/0013514 A1* 1/2020 Roy .................... A61B 8/10
2022/0378291 A1 12/2022 Sinha et al.
2023/0301514 A1 9/2023 Lepe et al.
2024/0389973 A1* 11/2024 Liu .................... A61B 8/08

FOREIGN PATENT DOCUMENTS

| KR | 10-2016-0037577 A | 4/2016 |
| KR | 10-2016-0114487 A | 10/2016 |
| KR | 10-2017-0116824 A | 10/2017 |
| KR | 10-2021-0061501 A | 5/2021 |
| KR | 10-2022-0019193 A | 2/2022 |
| KR | 10-2023-0028657 A | 3/2023 |
| KR | 10-2023-0050357 A | 4/2023 |

* cited by examiner

SYSTEM FOR MEASURING INTRAOCULAR PRESSURE

CROSS-REFERENCE TO RELATED APPLICATION

This application claims priority to and benefits under 35 U.S.C. § 119 of Korean Patent Application 10-2024-0059835 filed on May 7, 2024, in the Korean Intellectual Property Office (KIPO), the disclosure of which is incorporated by reference herein in its entirety.

BACKGROUND

1. Field

The present disclosure relates to an intraocular pressure measurement system, and more specifically, to an intraocular pressure measurement system that utilizes images of an internal structure of an eyeball of user obtained using a patch attached around the eyeball to measure intraocular pressure.

2. Description of the Related Art

The prevalence of neuro-pathological eye diseases is a significant public health issue. For example, glaucoma is one of the leading causes of blindness worldwide. Glaucoma refers to a group of eye diseases that damage the optic nerve. Abnormally high intraocular pressure (IOP) leads to glaucoma, which ultimately causes optic nerve degeneration and results in irreversible vision loss and blindness.

As such, increased intraocular pressure can lead to various eye diseases, such as glaucoma. Currently, the only practical method for treating glaucoma is to reduce intraocular pressure. Therefore, accurate measurement of intraocular pressure is critical for the prevention and treatment of various eye diseases, including glaucoma.

Meanwhile, in the past, pneumatic tonometry and applanation tonometry have been commonly used methods for measuring intraocular pressure. Pneumatic tonometry is a method of calculating intraocular pressure using the air flow rate and injection time when the cornea is flattened to a certain area by spraying a pneumatic pulse to the center of the cornea through an air spray nozzle. Applanation tonometry is a method of calculating intraocular pressure by directly compressing the center of the cornea with a prism and measuring the force required to flatten the cornea to a certain area.

However, the pneumatic tonometry tends to be less accurate, and applanation tonometry, which directly applies pressure to the cornea, can cause significant discomfort to the subject. Additionally, intraocular pressure can vary based on the inspection time and/or the subject's position, even for the same subject. Conventional pneumatic tonometry and applanation tonometry can only measure intraocular pressure at the moment of testing, failing to capture all medically significant biometric data.

SUMMARY

One or more embodiments of the present disclosure provide an intraocular pressure measurement system with improved examination convenience.

One or more embodiments of the present disclosure provide the intraocular pressure measurement system that is capable of measuring pressure at various locations within the eyeball.

One or more embodiments of the present disclosure provide the intraocular pressure measurement system that eliminates spatiotemporal constraints of intraocular pressure measurement by using a patch-type probe attached to the periphery of the eyeball.

One or more embodiments of the present disclosure provide the intraocular pressure measurement system that is capable of non-invasive and accurate measurement of intraocular pressure.

One or more embodiments of the present disclosure are not limited to the above-described aspects, and other technical aspects that are not described will be clearly understood by those skilled in the art from the following description.

In one or more embodiments of the present disclosure, an intraocular pressure measurement system is provided. The intraocular pressure measurement system comprises an ultrasound transmitter configured to generate a first driving signal and a second driving signal; a probe comprising a plurality of transducers, the probe configured to generate a first ultrasound signal based on the first driving signal, generate a second ultrasound signal based on the second driving signal, and irradiate the first ultrasound signal and the second ultrasound signal to an eyeball; an ultrasound receiver configured to receive an echo signal, which is the reflected second ultrasound signal, through the probe, and generate an ultrasound data based on the echo signal; and an image processing device configured to generate an image of an internal structure of the eyeball based on the ultrasound data, identify the internal structure of the eyeball based on the image of the internal structure of the eyeball, generate a point cloud data and a mesh data for the identified internal structure of the eyeball, calculate a stiffness of the identified internal structure of the eyeball, calculate a displacement of the internal structure of the eyeball according to the first ultrasound signal, and measure an intraocular pressure of the internal structure of the eyeball based on an acoustic radiation force according to the first ultrasound signal, a temporary deformation of the internal structure of the eyeball according to the first ultrasound signal, and a stiffness of the internal structure of the eyeball.

In an embodiment, the intraocular pressure measurement system further comprises a bending sensor configured to measure a curvature of the eyeball and generate a curvature information of the eyeball, wherein the image processing device generates the image of the internal structure of the eyeball by adjusting interference of the echo signal received by each of the plurality of transducers based on the curvature information of the eyeball.

In an embodiment, the ultrasound transmitter irradiates the first ultrasound signal to a cornea or a sclera of the eyeball, the ultrasound receiver receives a first echo signal generated from the cornea or a second echo signal generated from the sclera, and the image processing device measures the intraocular pressure of an anterior chamber using the ultrasound data generated based on the first echo signal, or measures the intraocular pressure of a vitreous cavity using the ultrasound data generated based on the second echo signal.

In an embodiment, the image processing device measures the intraocular pressure of the internal structure of the eyeball based on the relationship between velocity of a shear wave induced by the first ultrasound signal within the eyeball and stiffness of the internal structure of the eyeball.

In an embodiment, the probe, the ultrasound transmitter, and the ultrasound receiver are attached to the periphery of the eyeball or directly attached to the eyeball, and the image processing device is included in a mobile device.

Details of other embodiments are included in the detailed description and drawings.

According to one or more embodiments of the present disclosure, the intraocular pressure measurement system can increase the convenience of examination by measuring intraocular pressure based on the displacement of the eyeball induced by ultrasound.

According to one or more embodiments of the present disclosure, the intraocular pressure measurement system can measure the pressure at various locations within the eyeball by adjusting the position where displacement occurs inside the eyeball.

According to one or more embodiments of the present disclosure, the intraocular pressure measurement system can eliminate spatiotemporal limitations of intraocular pressure measurement by using a patch-type probe attached to the periphery of the eyeball.

According to one or more embodiments of the present disclosure, the intraocular pressure measurement system can accurately measure intraocular pressure non-invasively by using a patch-type probe attached to the periphery of the eyeball.

However, the effects of the present disclosure are not limited to the examples provided above, and a variety of other effects are included within the present disclosure, which can be further expanded within the scope of the present disclosure without departing from its principles.

BRIEF DESCRIPTION OF THE DRAWINGS

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

DETAILED DESCRIPTION

In the drawings, the thickness of certain lines, layers, components, elements or features may be exaggerated for clarity. It will be understood that, although the terms "first", "second", etc. may be used herein to describe various elements, these elements should not be limited by these terms. These terms are only used to distinguish one element from another element. Thus, a "first" element discussed below could also be termed a "second" element without departing from the teachings of the disclosure. As used herein, the singular forms are intended to include the plural forms as well, unless the context clearly indicates otherwise.

It will be further understood that the terms "includes" and/or "including", when used in this specification, specify the presence of stated features, integers, steps, operations, elements, and/or components, but do not preclude the presence and/or addition of one or more other features, integers, steps, operations, elements, components, and/or groups thereof.

In the entire specification, when an element is referred to as being "connected" or "coupled" to another element, it can be directly connected or coupled to the another element or be indirectly connected or coupled to the another element with one or more intervening elements interposed therebetween.

Further, an expression that an element such as a layer, region, substrate or plate is placed "on" or "above" another element indicates not only a case where the element is placed "directly on" or "just above" the other element but also a case where a further element is interposed between the element and the other element.

In the specification and the claims, the phrase "at least one of" is intended to include the meaning of "at least one selected from the group of" for the purpose of its meaning and interpretation. For example, "at least one of A and B" may be understood to mean "A, B, or A and B."

Hereinafter, embodiments of the disclosure will be described in more detail with reference to the accompanying drawings. Throughout the drawings, the same reference numerals are given to the same elements, and their descriptions will be omitted. <System According to Various Embodiments of the Present Disclosure>

Figure 1:
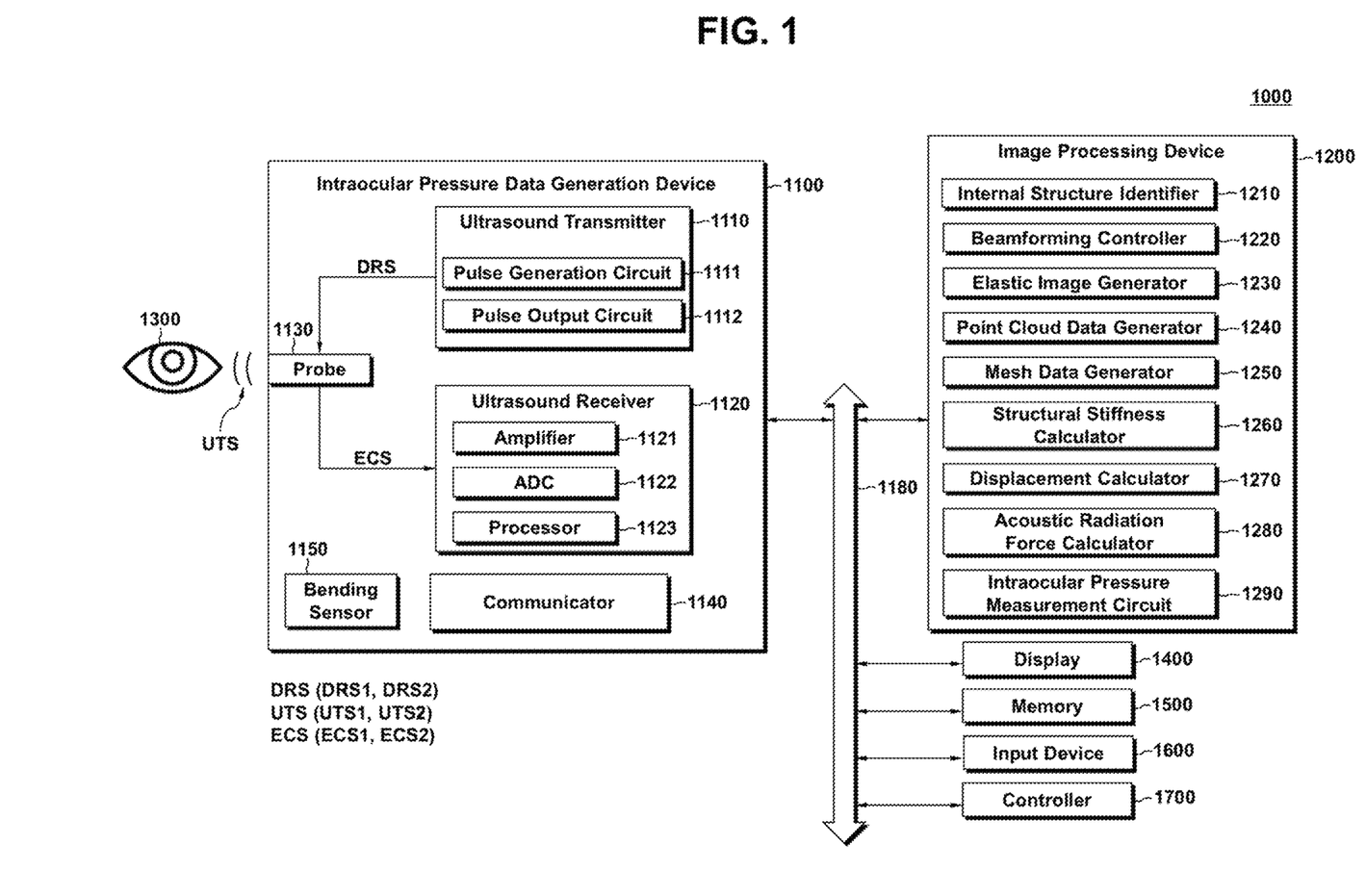
FIG. 1 is a block diagram of an intraocular pressure measurement system according to one or more embodiments of the present disclosure.

FIG. 1 is a block diagram of an intraocular pressure measurement system according to one or more embodiments of the present disclosure.

Figure 2:
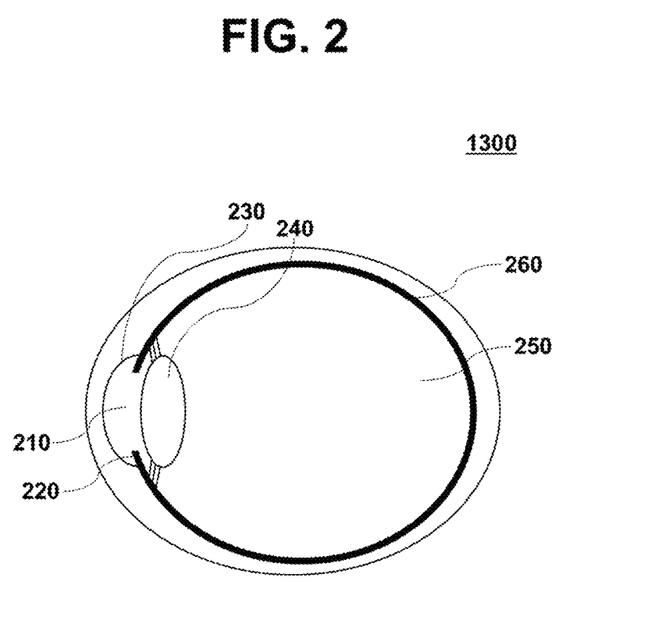
FIG. 2 is a diagram illustrating an internal structure of an eyeball.

FIG. 2 is a diagram illustrating an internal structure of an eyeball.

Figure 3:
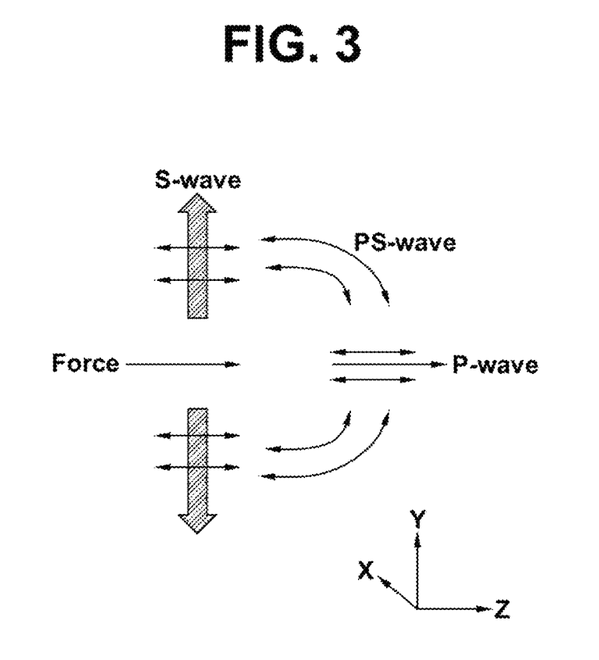
FIG. 3 is a diagram illustrating a shear wave.

FIG. 3 is a diagram illustrating a shear wave.

Figure 4:
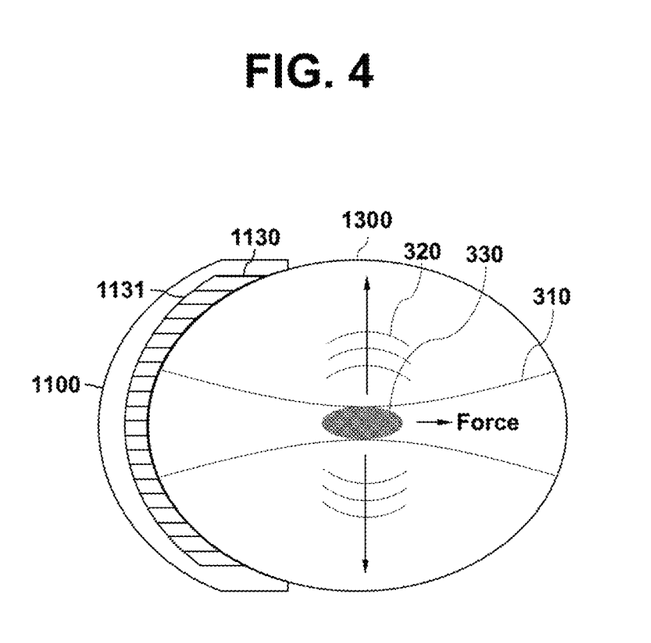
FIG. 4 is a diagram illustrating the shear wave generated within the eyeball.

FIG. 4 is a diagram illustrating the shear wave generated within the eyeball.

Referring to FIG. 1, the intraocular pressure measurement system 1000 according to embodiments of the present disclosure may measure intraocular pressure of an eyeball 1300 (e.g., an eyeball of user) using an image of an internal structure of the eyeball 1300 obtained using ultrasound.

The intraocular pressure measurement system 1000 may include an intraocular pressure data generation device 1100 and an image processing device 1200. In an embodiment, the intraocular pressure measurement system 1000 may further include a display 1400, a memory 1500, an input device 1600, a controller 1700 and a bus 1800. Various components of the intraocular pressure measurement system 1000 may be interconnected through the bus 1800.

The intraocular pressure data generation device 1100 may be attached to the periphery of the eyeball 1300, such as an eyelid or an area under the eye, and/or directly to the eyeball 1300. For example, the intraocular pressure data generation device 1100 may be a patch (e.g., an ultrasound patch) attached to the periphery of the eyeball 1300 and/or directly to the eyeball 1300.

By having the intraocular pressure data generation device 1100 in the form of a patch (e.g., ultrasound patch) attached to the periphery of the eyeball 1300 and/or directly to the eyeball 1300, the spatiotemporal constraints for measuring intraocular pressure are alleviated, providing ease of examination for the subject, while allowing for non-invasive and accurate measurement of the intraocular pressure.

Referring to FIG. 2 to explain the internal structure of the eyeball 1300 as a target for measuring intraocular pressure, the eyeball 1300 may include a cornea 230, an iris 220, and a lens 240, along with an anterior chamber 210 surrounded by the cornea 230, iris 220, and lens 240. The anterior chamber 210 may be filled with aqueous humor.

Additionally, the eyeball 1300 may include the vitreous body, which is located behind the lens 240 and maintains the shape of the eyeball 1300 within the sclera 260. Meanwhile, in the present disclosure, a space including the vitreous body may be referred to as a vitreous cavity 250.

In an embodiment, the intraocular pressure data generation device 1100 may generate intraocular pressure data (e.g., ultrasound data) related to the anterior chamber 210 or vitreous cavity 250. The image processing device 1200 may measure the intraocular pressure of the anterior chamber 210 or vitreous cavity 250.

Referring to FIG. 1, the intraocular pressure data generation device 1100 may generate the intraocular pressure data and provide the generated intraocular pressure data to the image processing device 1200. For example, the intraocular pressure data generation device 1100 may acquire the intraocular pressure data, such as ultrasound data, from the eyeball 1300 and provide the obtained data (e.g., ultrasound data) to the image processing device 1200.

In an embodiment, the intraocular pressure data generation device 1100 may include an ultrasound transmitter 1110, an ultrasound receiver 1120, a probe 1130, and a communicator 1140. In some embodiments, the intraocular pressure data generation device 1100 may further include a bending sensor 1150.

For example, the probe 1130 may be an ultrasound probe. As an example, the probe 1130 may include at least one of a linear array probe, curved array probe, phased array probe and volume probe. However, the embodiments of the present disclosure are not limited to these types of probes, and the probe 1130 may include various probes such as an endocavity probe, convex probe, matrix probe, or 3D probe.

The probe 1130 may generate an ultrasound signal UTS based on a driving signal DRS provided by the ultrasound transmitter 1110 (e.g., pulse output circuit 1112). For example, the probe 1130 may include a plurality of transducers.

Each of the plurality of transducers may vibrate according to the driving signal DRS in the form of electromagnetic energy and convert the driving signal DRS into the ultrasonic signal UTS in the form of acoustic energy, which is mechanical energy. For example, the plurality of transducers included in the probe 1130 may include, but is not limited to, piezoelectric and/or magnetically contractile materials.

The ultrasound transmitter 1110 may supply the driving signal DRS to the probe 1130. For example, the ultrasound transmitter 1110 may provide a first driving signal DRS1 and a second driving signal DRS2 to the probe 1130. The probe 1130 may generate a first ultrasound signal UTS1 based on the first driving signal DRS1 and a second ultrasound signal UTS2 based on the second driving signal DRS2. The first ultrasound signal UTS1 may be referred to as a push pulse (or push ultrasound signal), and the second ultrasound signal UTS2 may be referred to as an observation signal (or observation ultrasound signal).

In an embodiment, the ultrasound transmitter 1110 may include a pulse generation circuit 1111 and a pulse output circuit 1112.

The pulse generation circuit 1111 may generate a plurality of pulses for generating a transmission ultrasonic wave, for example, the ultrasonic signal UTS, according to a predetermined pulse repetition frequency (PRF).

In an embodiment, the pulse generation circuit 1111 may determine an amplitude adjustment value and/or a phase adjustment value for determining transmission directionality for each of the plurality of pulses, and apply the determined amplitude adjustment value and/or phase adjustment value to each of the plurality of pulses. For example, each pulse with corresponding amplitude adjustment value and/or phase adjustment value may correspond to each of the plurality of transducers included in the probe 1130.

The pulse output circuit 1112 may apply the corresponding beamforming control value (or ultrasound transmission control value) to each of the plurality of pulses. Accordingly, the pulse output circuit 1112 may apply the first driving signal DRS1 to the probe 1130 so that each pulse to which the corresponding beamforming control value (or ultrasonic transmission control value) is applied is generated. In other words, the pulse generation circuit 1111 and the pulse output circuit 1112 may perform a beamforming operation for improving the resolution of an ultrasound image and controlling an acoustic radiation force by appropriately adjusting the phase and/or amplitude so that the plurality of pulses included in the first ultrasonic signal UTS1 transmitted by each of the plurality of transducers included in the probe 1130 are simultaneously focused on one focal point. This beamforming operation in which the plurality of pulses included in the first ultrasound signal UTS1 are simultaneously focused on one focal point enhances the resolution of the ultrasound image because the amount of tissue movement of the eyeball 1300 may be relatively increased and become more uniform.

In an embodiment, the beamforming control value (or ultrasound transmission control value) applied to the plurality of pulses may be extracted (computed, calculated, or generated) by the beamforming controller. A detailed explanation of this will be provided later.

The probe 1130 may generate the first ultrasound signal UTS1 in the form of a push pulse (or push ultrasound signal) based on the first driving signal DRS1 provided from the ultrasound transmitter 1110 (e.g., the pulse output circuit 1112). The probe 1130 may irradiate the first ultrasound signal UTS1 to the region of interest (ROI) of the eyeball 1300. For example, the region of interest of the eyeball 1300 may be located within the cornea 230 or the sclera 260, but is not limited thereto.

The first ultrasound signal UTS1 in the form of a push pulse may induce deformation of the tissue within the eyeball 1300 and induce generation of a shear wave, for example, a transverse wave.

To explain the shear wave, referring to FIG. 3, when the force of the push pulse is applied along the Z-axis direction, a longitudinal wave (P-wave), a transverse wave (S-wave), and a PS-wave formed from the coupling of P-wave and S-wave may be generated. The shear wave may refer to a wave that vibrates in the wave propagation direction from the vibration source to which the force is applied and propagates in the Y-axis direction, and may mean the S-wave.

When the first ultrasound signal UTS1 in the form of a push pulse is irradiated to the eyeball 1300, deformation (e.g., temporary deformation) of the tissue within the eyeball 1300 may be induced, and generation of the shear wave (e.g., the transverse wave) may be induced.

For example, referring further to FIG. 4, the intraocular pressure data generation device 1100 may irradiate a focused first ultrasound signal UTS1 (hereinafter, referred to as "focused beam 310") to the eyeball 1300 to push at least a portion of the eyeball 1300. For example, the intraocular pressure data generation device 1100 may irradiate the focused beam 310 with a long wavelength toward the eyeball 1300 using at least one of the plurality of channels, such as the plurality of transducers 1131, included in the probe 1130.

The focused beam 310 may be irradiated to a focal point 330 within the region of interest and may induce deformation (e.g., temporary deformation) of the eyeball 1300. In other words, when a force is applied in the depth direction to the focal point 330 by the focused beam 310, the tissue of the eyeball 1300 at the focal point 330 moves in the depth direction. The magnitude and direction of the force applied to the focal point 330 may be determined based on beamforming conditions (e.g., beamforming conditions based on the aforementioned beamforming control value or ultrasound transmission conditions based on ultrasound transmission control value). The distance that each point within the tissue of the eyeball 1300 moves due to the applied force may be defined as displacement. Since the tissue has a certain elasticity, and adjacent tissues are organically connected, the movement of tissue at the focal point 330 may affect the adjacent tissue. Therefore, displacement of the tissue adjacent to the focal point 330 may be induced.

In this case, the shear wave 320 may be propagated in a transverse direction defined according to the local curvature of the tissue near the focal point 330 by the focused beam 310 in tissue of the eyeball 1300. For example, the shear wave 320 may be propagated at a speed of about 1 m/s to 10 m/s, but is not limited thereto.

Referring again to FIG. 1, the pulse generation circuit 1111 may generate a second driving signal DRS2 to generate the observation signal (e.g., a second ultrasonic signal UTS2) that is irradiated to the region of interest to observe the transverse wave induced by the push pulse (e.g., the first ultrasonic signal UTS1).

The probe 1130 may transmit the second ultrasound signal UTS2 to the eyeball 1300 to observe the transverse wave induced by the first ultrasound signal UTS1 in response to the second driving signal DRS2 provided by the ultrasound transmitter 1110, and receive an echo signal ECS reflected from the eyeball 1300.

In an embodiment, as previously described, in order for the intraocular pressure data generation device 1100 to measure intraocular pressure in the anterior chamber 210 or vitreous cavity 250, the probe 1130 may receive a first echo signal ECS1 generated from the cornea 230 of the eyeball 1300 and a second echo signal ECS2 generated from the sclera 260 of the eyeball 1300. In some embodiments, depending on the type of intraocular pressure to be measured, the intraocular pressure data generation device 1100 may selectively receive at least one of the first echo signal ECS1 and the second echo signal ECS2, but is not limited thereto.

In an embodiment, the ultrasound transmitter 1110 may further include an ultrasonic waveform control circuit, such as a pulse width modulation (PWM) circuit and a phase-locked loop (PLL) circuit. The pulse generation circuit 1111 may use the ultrasonic waveform control circuit to precisely control the frequency and intensity of the ultrasound signal.

In an embodiment, the ultrasound transmitter 1110 may receive curvature information related to the curvature of the eyeball 1300 and/or adnexa from the bending sensor 1150. Based on the curvature information, the ultrasound transmitter 1110 may generate the focused beam 310 by adjusting the phase and/or amplitude of the plurality of ultrasound signals UTS output by each of the plurality of transducers 1131. Accordingly, during the process of generating the ultrasound image, the curvature information may help improve crosstalk resulting from signal interference between the plurality of ultrasound signals UTS output by the plurality of transducers 1131. Additionally, the precision of controlling the acoustic radiation force by the focused beam 310 may be improved.

The ultrasound receiver 1120 may process the echo signal ECS (e.g., the first echo signal ECS1 and/or the second echo signal ECS2) received by the probe 1130, and generate ultrasound data. For this purpose, in an embodiment, the ultrasound receiver 1120 may include an amplifier 1121, an analog digital converter (ADC) 1122, and a processor 1123.

The amplifier 1121 may amplify the echo signal ECS received by each channel, and the ADC 1122 may convert the amplified echo signal ECS from analog to digital for each channel. The processor 1123 may apply the amplitude adjustment value and/or phase adjustment value for determining the reception directionality to the converted digital echo signal ECS and then generate the ultrasound data by summing the echo signal ECS.

Meanwhile, the plurality of channels may correspond to each of the plurality of transducers 1131. Accordingly, the amplifier 1121 and the ADC 1122 may be formed corresponding to each of the plurality of transducers 1131, but are not limited thereto.

Meanwhile, in some embodiments, the ultrasound receiver 1120 may not include the amplifier 1121 depending on its implementation. For example, if the sensitivity of the probe 1130 is enhanced, or if the bit-depth of the ADC 1122 is increased, the amplifier 1121 may be omitted.

The intraocular pressure data generation device 1100 may irradiate the ultrasound signal UTS into each tissue of the eyeball 1300, receive the echo signal ECS, such as reflected signal, and provide the echo signal ECS as the ultrasound data to the image processing device 1200 via the communicator 1140.

Additionally, in an embodiment, the intraocular pressure data generation device 1100 may irradiate the focused beam 310 to each tissue in the eyeball 1300 as the focal point 330, receive echo signal ECS, such as reflected signal, for the focused beam 310, and provide the echo signal ECS as the ultrasound data to the image processing device 1200 through the communicator 1140.

In an embodiment, the processor 1123 may generate improved ultrasound data by correcting interference between the plurality of echo signals ECS based on the curvature information of the eyeball 1300 and/or adnexa. For example, the processor 1123 may extract (generate, or calculate) information related to the configuration of the plurality of transducers 1131 based on the curvature information of the eyeball 1300 and/or adnexa. Based on this information related to the configuration, the processor 1123 may use this information to dynamically adjust delay times to reduce crosstalk, and/or apply beamforming. Beamforming may include delay-and-sum beamforming, adaptive beamforming, multi-beamforming, micro beamforming, synthetic aperture beamforming, etc. In some embodiments, the curvature information of the eyeball 1300 may be provided by, but is not limited to, the bending sensor 1150.

The communicator 1140 may provide ultrasound data to the image processing device 1200. The communicator 1140 may include one or more components that enable communication with external devices. For example, the communicator 1140 may include at least one of a short-range communication module, wired communication module, and wireless communication module. The short-range communication module may refer to a module for short-range communication within a specific range. For example, short-range communication technologies may include Wireless LAN, Wi-Fi, Bluetooth, ZigBee, WFD (Wi-Fi Direct), UWB (ultra-wideband), infrared communication (IrDA, infrared Data Association), BLE (Bluetooth Low Energy), and NFC (Near Field Communication), but are not limited to. The wired communication module may refer to a module that uses electrical or optical signals for communication. For example, wired communication technologies may include, but are not limited to, twisted pair cable, coaxial cable, fiber optic cable, and ethernet cable. Mobile communication module may send and receive wireless signals from at least one of a base station, external terminal, or server on a mobile network. These wireless signals may include various forms of data according to voice call signals, video call signals, or text/multimedia message transmission.

The bending sensor 1150 may sense the curvature information of the eyeball 1300. The bending sensor 1150 may be attached to the periphery of the eyeball 1300, such as the eyelid or under-eye area. In some embodiments, the bending sensor 1150 may be attached along with the ultrasound transmitter 1110 and ultrasound receiver 1120 to the periphery of the eyeball 1300. The communicator 1140 may receive the curvature information of the eyeball 1300 from the bending sensor 1150 and provide the curvature information of the eyeball 1300 to the image processing device 1200.

For example, the bending sensor 1150 may have a characteristic of bending itself, and sense the curvature of the eyeball 1300 by utilizing the property that the electrical characteristic value (e.g., resistance, capacitance, etc.) changes depending on the degree of bending. As an example, the bending sensor 1150 may include an optical fiber bend sensor, pressure sensor, or strain gauge, etc., but is not limited thereto.

Additionally, as described above, the curvature information of the eyeball 1300 sensed by the bending sensor 1150 may be provided to the ultrasound transmitter 1110, the processor 1123 included in the ultrasound receiver 1120, and/or the image processing device 1200.

According to an exemplary embodiment of the present disclosure, by using the curvature information of the eyeball 1300 generated by the bending sensor 1150, the ultrasound transmitter 1110 may adjust the phase and/or amplitude between the plurality of ultrasound signals UTS, and/or the processor 1123 may correct interference between the plurality of echo signals ECS. Thus, the intraocular pressure measurement test using the intraocular pressure measurement system 1000 according to one of more embodiments of the present disclosure is not dependent on the curvature of the cornea of the eyeball 1300. Therefore, accurate intraocular pressure measurements can be performed even for the subjects who have undergone surgical procedures like LASIK, LASEK, cataract surgery, or those with physiological changes in the cornea due to aging or the development of myopia. Meanwhile, although the above description is based on the processor 1123 correcting interference between the plurality of echo signals ECS, the embodiments of the present disclosure are not limited thereto. For example, in some embodiments, the image processing device 1200 described below may correct interference between the plurality of echo signals ECS by using the curvature information of the eyeball 1300 generated from the bending sensor 1150.

In an embodiment, an insulator may be disposed between the bending sensor 1150 and the ultrasound transmitter 1110, or between the bending sensor 1150 and the probe 1130, to reduce electromagnetic interference. The insulator may include an insulating material. For example, the insulator may include, but is not limited to, an inorganic or organic insulating material.

The image processing device 1200 may include an internal structure identifier 1210, a beamforming controller 1220, an elastic image generator 1230, a point cloud data generator 1240, a mesh data generator 1250, a structural stiffness calculator 1260, a displacement calculator 1270, an acoustic radiation force calculator 1280, and an intraocular pressure measurement circuit 1290.

The internal structure identifier 1210 may identify the internal structure of the eyeball 1300 based on the obtained ultrasound data (e.g., ultrasound image). Specifically, the internal structure identifier 1210 may determine the boundary of the internal structure included in the region of interest of the eyeball 1300, and perform labeling on the internal structure with the shape of the determined boundary. For example, the internal structure identifier 1210 may determine the boundary of the cornea 230 and/or sclera 260 in the eyeball 1300 from the ultrasound data (e.g., ultrasound image), but is not limited thereto.

The beamforming controller 1220 may extract (or calculate, compute, generate) an optimal ultrasound transmission control value (or beamforming control value) to enable the acoustic radiation force to be intensively applied in the direction of the intended force to the region of interest (e.g., cornea 230 and/or sclera 260, etc.) of the eyeball 1300 identified by the internal structure identifier 1210.

In an embodiment, the beamforming controller 1220 may digitize the data (e.g., data related to the internal structure included in the region of interest of the eyeball 1300) obtained from the internal structure identifier 1210, a direction of the acoustic radiation force to be applied, an array structure of the plurality of transducers 1131 (e.g., an arrangement of the plurality of transducers 1131), and the acoustic properties of the tissues in the eyeball 1300, etc., and extract (or calculate, generate) the suitable ultrasound signal transmission condition (or beamforming control value) using a trained artificial intelligence model. For example, the beamforming controller 1220 may control the intraocular pressure data generation device 1100 (e.g., the ultrasound transmitter 1110 and probe 1130) to transmit the ultrasonic signal UTS with varying frequencies. As an example, the beamforming controller 1220 may input the echo signal ECS according to a change in frequency as time series data or data in a format converted through mathematical transformation, along with the conditions of the acoustic radiation force to be applied and the array structure of the plurality of transducers 1131, into a deep neural network (DNN) trained through reinforcement learning. For example, the mathematical transform may include at least one of various known mathematical transforms, such as a wavelet transform, a Fourier transform, a short time Fourier transform, a discrete cosine transform, a Laplace transform, a Z-transform, a Hilbert transform, a Mellin transform, a Hartley transform, and a fractional Fourier transform, etc.

Additionally, the deep neural network, after receiving the data described above, may extract latent vectors representing the acoustic properties of the tissue. Considering the array structure of the plurality of transducers 1131 and the conditions for applying acoustic radiation force, the deep neural network may extract the ultrasound signal transmission conditions (or beamforming control value) that maximize the similarity of a function representing the generated acoustic radiation force field and the conditions for the acoustic radiation force to be applied. The function representing the acoustic radiation force conditions may include at least one of the point spread function, line spread function, edge spread function, impulse response function, Bessel function, Zernike polynomial, and Voigt profile.

Meanwhile, the above description has been made based on the beamforming controller 1220 extracting the ultrasound signal transmission condition (or beamforming control value) using the deep neural network (DNN) trained through reinforcement learning, but the embodiments of the present disclosure are not limited thereto. For example, the learned artificial intelligence model may include at least one of the various artificial neural networks described below, and may be trained using at least one of the various artificial intelligence learning paradigms described below.

According to an exemplary embodiment, the artificial intelligence model may be trained through a separate processor included in the intraocular pressure measurement system 1000. Here, the separate processor may include a hardware structure specialized for processing the artificial intelligence model. The artificial intelligence model may be generated through machine learning. The machine learning may refer to training that optimizes parameters with given data using a model composed of a plurality of parameters. Such training may be performed, for example, in the electronic device 100 itself on which the artificial intelligence is performed, but is not limited thereto. The artificial intelligence training paradigm may refer to various learning methods and approaches, and may include, for example, supervised learning, weakly supervised learning, unsupervised learning, semisupervised learning, reinforcement learning, self-supervised learning, or transfer learning. For example, artificial intelligence learning algorithms may include, but are not limited to, linear regression, logistic regression, decision trees, random forests, Gaussian processes, support vector machines (SVM), or artificial neural networks. The artificial neural network may be one of a deep neural network (DNN), a convolutional neural network (CNN), a deep convolutional neural network (DCNN), a recurrent neural network (RNN), a generative adversarial network (GAN), a restricted Boltzmann machine (RBM), a deep belief network (DBN), a bidirectional recurrent deep neural network (BRDNN), deep Q-networks, a feedforward algorithm, a transformer, a Bayesian neural network, or a combination of two or more of the above, but is not limited to the examples described above. The artificial intelligence model may include a plurality of artificial neural network layers. In addition to or as an alternative to a hardware structure, the artificial intelligence model may include a software structure.

In the above, the separate processor may be included in the intraocular pressure measurement system 1000, and the artificial intelligence may be performed in the intraocular pressure measurement system 1000 itself. However, the embodiment of the present disclosure is not limited thereto. For example, the artificial intelligence learning may be performed in a separate server. As an example, the artificial intelligence model may be trained by an external processor and then stored in the memory 1500.

The elastic image generator 1230 may generate an elastic image through a scan conversion process for the ultrasound data. The elastic image generator 1230 may calculate the velocity of the transverse wave based on the ultrasound data. For example, the elastic image generator 1230 may calculate the velocity of the transverse wave generated by displacement of the tissues in the eyeball 1300 from the ultrasound data. Since the velocity of transverse wave propagation varies depending on the stiffness of the tissue, the stiffness of the tissue can be calculated using the velocity of transverse wave.

Referring further to FIG. 4, since the velocity of the first ultrasonic signal UTS1 (e.g., the shear wave 320 induced by the focused beam 310) is very slow compared to the average velocity (e.g., approximately 1540 m/s) of the ultrasonic signal within the eyeball 1300, as described above, the intraocular pressure data generation device 1100 may utilize the second ultrasonic signal UTS2 (or, observation signal) to track and/or observe the shear wave 320. For example, the intraocular pressure data generation device 1100 may track the velocity of the shear wave 320 by transmitting the second ultrasonic signal UTS2 in the direction of propagation of the shear wave 320. At this time, the wavelength of the second ultrasonic signal UTS2 for tracking and/or observing the shear wave 320 may be shorter than the wavelength of the focused beam 310. The velocity of the shear wave 320 may change depending on the vibrational characteristics of the medium. Therefore, the mechanical characteristic values of the target object may be obtained by estimating the velocity of the shear wave 320.

In order to estimate the velocity of the transverse wave, the ultrasound transmitter 1110 may irradiate the focused beam 310 and then irradiate the second ultrasound signal UTS2, which is the observation signal, to the eyeball 1300. In other words, the ultrasound transmitter 1110 may irradiate the second ultrasound signal UTS2 with a wide beam profile to the region of interest where the tissue displacement occurs and the shear wave 320 is traveling, and the ultrasound receiver 1120 may receive the echo signal ECS of the second ultrasound signal UTS2 reflected from the region of interest. Accordingly, the elastic image generator 1230 may detect the displacement of the tissue based on the echo signal ECS.

In an embodiment, the elastic image generated by the elastic image generator 1230 may refer to an image of a gray scale obtained by scanning the object in A mode (amplitude mode), B mode (brightness mode), and M mode (motion mode), as well as an image expressing a dynamic object using a Doppler effect or a deformation measurement algorithm.

For example, the elastic image generator 1230 may extract and process a B mode component from the ultrasound data. The elastic image generator 1230 may generate the elastic image in which the intensity of the signal is expressed as brightness based on the extracted B mode component.

As another example, the elastic image generator 1230 may extract a Doppler component from the ultrasound data and generate a Doppler image expressing the movement of the object in color or waveform based on the extracted Doppler component.

As another example, the elastic image generator 1230 may form an image from the ultrasound data and generate an acoustic force impulse image to which an image processing algorithm suitable for deformation measurement is applied.

According to an exemplary embodiment, the elastic image generator 1230 may generate a three-dimensional ultrasound image through a volume rendering process for volume data, and may generate the elastic image that visualizes the degree of deformation of the eyeball 1300 according to pressure. Furthermore, the elastic image generator 1230 may express various additional information on the ultrasound image as text or graphics. Meanwhile, the generated ultrasound image may be stored in the memory 1500.

In an embodiment, the elastic image generator 1230 may generate the ultrasound image with improved resolution by removing interference components between echo signals ECS based on the curvature information of the eyeball 1300.

The point cloud data generator 1240 may generate point cloud data based on the ultrasound data. The point cloud data may refer to data representing a set of multiple points spread over a three-dimensional space. The point cloud data may be data generated for data weight reduction by performing image segmentation on the region of interest of the eyeball 1300 based on the ultrasound image acquired in a previous process. The point cloud data may be data representing a structural shape of eyeball tissue.

In an embodiment, the point cloud data generator 1240 may generate the point cloud data corresponding to the plurality of tissues based on echo signals ECS of ultrasound signals irradiated to each tissue by the probe 1130.

The mesh data generator 1250 may generate mesh data for the internal structure of the eyeball 1300 based on the point cloud data. For example, the mesh data generator 1250 may generate mesh data by performing a smoothing operation that excludes points unrelated to the shape of the internal structure of the eyeball 1300 among the plurality of points and connecting some of the remaining points. However, the embodiment of the present disclosure is not limited thereto. For example, since the shape of the tissue of the eyeball 1300 is generally standardized, the mesh data generator 1250 may use the information included in the point cloud data to transform the mesh in the form of a pre-stored template and use it as is. Meanwhile, the mesh in the form of the pre-stored template may be stored in the memory 1500, but is not limited thereto.

In an embodiment, the mesh data generator 1250 may generate the mesh data for a portion of the structure of the eyeball 1300. For example, the mesh data generator 1250 may generate mesh data corresponding to the cornea 230 and/or the sclera 260 of the eyeball 1300.

In an embodiment, the mesh data generator 1250 may perform the smoothing operation to exclude points that are unrelated to the shape of the internal structure of the eyeball 1300 based on the curvature information of the eyeball 1300.

The structural stiffness calculator 1260 may calculate the stiffness of the identified internal structure. For example, the structural stiffness calculator 1260 may determine the overall geometric shape of the internal structure and the type of tissue comprising the internal structure, and determine the structural dynamic stiffness of the internal structure of the eyeball 1300 based on the geometric shape and the stiffness of the tissue.

The displacement calculator 1270 may calculate the displacement of the entire or a part of the eyeball 1300 from the elastic image generated by the elastic image generator 1230 or the mesh data generated by the mesh data generator 1250. For example, the displacement calculator 1270 may calculate the displacement by comparing the echo signal ECS before and after the first ultrasonic signal UTS1, which is a push pulse, is irradiated to the eyeball 1300, or by comparing the ultrasonic data derived from the echo signal ECS.

The acoustic radiation force calculator 1280 may calculate the acoustic radiation force by the first ultrasonic signal UTS1. An example of a method of calculating the acoustic radiation force will be described in more detail with reference to FIG. 5.

The intraocular pressure measurement circuit 1290 may measure the intraocular pressure based on the stiffness of the internal structure of the eyeball 1300, the displacement of the eyeball 1300 by the first ultrasonic signal UTS1, and the acoustic radiation force of the first ultrasonic signal UTS1.

In an embodiment, with respect to the internal structure having the calculated stiffness, the intraocular pressure measurement circuit 1290 may compare the theoretical displacement that occurs when the calculated acoustic radiation force is applied with the actual displacement of the eyeball 1300 measured through the ultrasonic data, and calculate the intraocular pressure based on the difference in displacement. For example, the intraocular pressure measurement circuit 1290 may calculate a relatively low intraocular pressure when the theoretical displacement is greater than the actual displacement, and may calculate a relatively high intraocular pressure when the theoretical displacement is smaller than the actual displacement.

In an embodiment, with respect to the internal structure having the calculated stiffness, the intraocular pressure measurement circuit 1290 may measure temporary deformation of the tissue of the eyeball 1300 caused by the applied acoustic radiation force through ultrasound data. For example, the intraocular pressure measurement circuit 1290 may calculate the intraocular pressure by comparing and analyzing the work caused by the external force applied to the tissue such as the calculated acoustic radiation force and the intraocular pressure and the internal energy generated thereby. In some embodiments, in order to measure the intraocular pressure more accurately, the intraocular pressure measurement circuit 1290 may calculate the intraocular pressure by further considering the energy loss of the tissue having viscoelastic characteristics and the prestress existing in the tissue. In addition, the intraocular pressure measurement circuit 1290 may make complex modeling and accurate measurement possible by applying different magnitudes and directions of acoustic radiation force to the same region of interest of the eyeball 1300.

Accordingly, the intraocular pressure measurement system 1000 according to one or more embodiments of the present disclosure may measure the intraocular pressure by using temporary deformation of the tissue of the eyeball 1300 due to the ultrasonic signal UTS, so that the convenience of examination can be improved.

In an embodiment, the structural stiffness calculator 1260 may calculate the stiffness of the internal structure of the eyeball 1300 based on the velocity of the transverse wave generated by the elastic image generator 1230. The intraocular pressure measurement circuit 1290 may measure the intraocular pressure based on the stiffness of the internal structure of the eyeball 1300 calculated by the structural stiffness calculator 1260, the stiffness calculated based on the velocity of the transverse wave, the displacement of the eyeball 1300 by the first ultrasonic signal UTS1, and the acoustic radiation force of the first ultrasonic signal UTS1.

In an embodiment, with respect to the internal structure of the eyeball 1300, the intraocular pressure measurement circuit 1290 may calculate the intraocular pressure through an optimization algorithm that finds the magnitude of the hydrostatic pressure that allows the combined force (or resultant force, net force) of the internal force and the external force to be balanced by considering the inertial force.

In an embodiment, the intraocular pressure data generation device 1100 may generate the first ultrasonic data based on the first echo signal ECS1 generated from the cornea 230. The image processing device 1200 may measure the intraocular pressure of the anterior chamber 210 based on the first ultrasound data.

In addition, in an embodiment, the intraocular pressure data generation device 1100 may generate the second ultrasound data based on the second echo signal ECS2 generated from the sclera 260. The image processing device 1200 may measure the intraocular pressure of the vitreous cavity 250 based on the second ultrasound data.

Meanwhile, the above description is based on the intraocular pressure measurement system 1000 measuring the intraocular pressure of the anterior chamber 210 and/or the vitreous cavity 250 based on ultrasound data (e.g., the first ultrasound data and/or the second ultrasound data) generated based on echo signals ECS (e.g., first echo signal ECS1 and/or second echo signal ECS2) generated from the cornea 230 and/or the sclera 260 within the eyeball 1300. However, this is exemplary, and the intraocular pressure measurement system 1000 according to one or more embodiments of the present disclosure may measure the intraocular pressure at various locations within the eyeball 1300.

The intraocular pressure measurement system 1000 according to one or more embodiments of the present disclosure may measure pressure (e.g., intraocular pressure) corresponding to various positions within the eyeball 1300 by freely adjusting the position where displacement occurs within the eyeball 1300.

The display 1400 may display and output the generated ultrasound images and intraocular pressure information. The display 1400 may display and output various information processed in the intraocular pressure measurement system 1000 on the screen through a GUI (Graphical User Interface). Meanwhile, the intraocular pressure measurement system 1000 may include two or more displays 1400 depending on the implementation form.

The memory 1500 may store various information processed in the intraocular pressure measurement system 1000. For example, the memory 1500 may store input/output ultrasound data, ultrasound images, information on intraocular pressure, information on the internal structure of the eyeball 1300, information on the stiffness of the internal structure of the eyeball 1300, information on an algorithm for calculating acoustic radiation force, information on an algorithm for measuring intraocular pressure, etc.

For example, the memory 1500 may be implemented as various types of storage media such as flash memory, a hard disk, and an EEPROM. Meanwhile, in some embodiments, the intraocular pressure measurement system 1000 may also operate a web storage or cloud server that performs the storage function of the memory 1500 on the web.

The input device 1600 may receive data from a user for controlling the intraocular pressure measurement system 1000. For example, the input device 1600 may include hardware configurations such as a key pad, a mouse, a touch pad, a touch screen, a trackball, a jog switch, etc., but is not limited thereto, and may further include various input devices such as an electrocardiogram measurement module, a respiration measurement module, a voice recognition sensor, a gesture recognition sensor, a fingerprint recognition sensor, an iris recognition sensor, a depth sensor, a distance sensor, etc.

The controller 1700 may control the overall operation of the intraocular pressure measurement system 1000.

According to an exemplary embodiment, the image processing device 1200, the display 1400, the memory 1500, the input device 1600, and the controller 1700 may be configured as separate devices from the intraocular pressure data generation device 1100 as a mobile device or a host device. However, the embodiments of the present disclosure are not limited thereto. For example, components of the intraocular pressure measurement system 1000 may be at least partially included in one device.

<Relationship Between the Distance from a Source of a Focused Beam and the Intensity of the Focused Beam>

Figure 5:
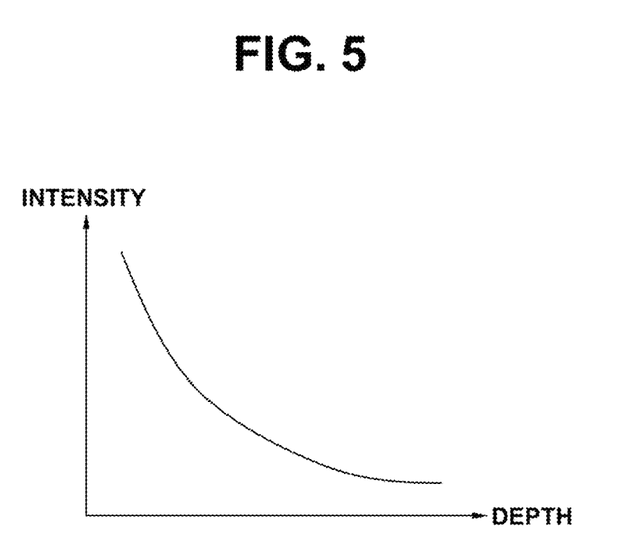
FIG. 5 is a diagram illustrating the relationship between the distance from a source of a focused beam and the intensity of the focused beam.

FIG. 5 is a diagram illustrating the relationship between the distance from a source of a focused beam and the intensity of the focused beam.

In FIG. 5, the horizontal axis may represent the distance (DEPTH) from the source of the focused beam 310, and the vertical axis may represent the intensity (INTENSITY) of the focused beam 310.

Referring to FIGS. 1, 4, and 5, when the probe 1130 induces the displacement of the eyeball 1300 using the focused beam 310, the intensity of the focused beam 310 may be adjusted by frequency. When the medium is uniform and the ultrasound is radiated in the form of a plane wave, the acoustic radiation force involved in causing the displacement may be proportional to the intensity.

The acoustic radiation force generated by the plane wave passing through the uniform medium may be calculated by the following equation 1. In cases where the aforementioned assumptions are not met, the acoustic radiation force may be calculated based on computational analysis rather than the analytical formula below.

$$F = \frac{2\alpha I}{c} \qquad \text{[Equation 1]}$$

In equation 1, "F" represents the acoustic radiation force, "I" represents the intensity of the focused beam 310, "c" represents the velocity of ultrasound, and "a" represents the attenuation coefficient.

Additionally, in the case of the plane wave passing through the uniform medium, the intensity of the focused beam 310 at position x may be calculated using the following equation 2.

$$I(x) = I_0 \times e^{-\alpha f x} \qquad \text{[Equation 2]}$$

In equation 2, "I(x)" represents the intensity of the focused beam 310 at position x, "$I_0$" represents the intensity of the focused beam 310 output from the probe 1130, "e" represents a natural constant (Euler's number), "α" represents the attenuation coefficient, "f" represents the frequency, and "x" represents the depth.

In an embodiment, the acoustic radiation force calculator 1280 may calculate the acoustic radiation force at various locations within the eyeball 1300 by utilizing the above equations 1 and 2.

The invention claimed is:

1. An intraocular pressure measurement system comprising:
an ultrasound transmitter configured to generate a first driving signal and a second driving signal;
a probe comprising a plurality of transducers, the probe configured to:
generate a first ultrasound signal based on the first driving signal;
generate a second ultrasound signal based on the second driving signal; and
irradiate the first ultrasound signal and the second ultrasound signal to an eyeball;
an ultrasound receiver configured to receive an echo signal, which is the reflected second ultrasound signal, through the probe, and generate an ultrasound data based on the echo signal; and
an image processing device configured to:
generate an image of an internal structure of the eyeball based on the ultrasound data;

identify the internal structure of the eyeball based on the image of the internal structure of the eyeball;

generate a point cloud data and a mesh data for the identified internal structure of the eyeball;

calculate a stiffness of the identified internal structure of the eyeball;

calculate a displacement of the internal structure of the eyeball according to the first ultrasound signal; and measure an intraocular pressure of the internal structure of the eyeball based on an acoustic radiation force according to the first ultrasound signal, a temporary deformation of the internal structure of the eyeball according to the first ultrasound signal, and a stiffness of the internal structure of the eyeball, wherein the ultrasound transmitter irradiates the first ultrasound signal to a cornea or a sclera of the eyeball, wherein the ultrasound receiver receives a first echo signal generated from the cornea or a second echo signal generated from the sclera, and wherein the image processing device measures the intraocular pressure of an anterior chamber using the ultrasound data generated based on the first echo signal, or measures the intraocular pressure of a vitreous cavity using the ultrasound data generated based on the second echo signal.

2. The intraocular pressure measurement system of claim 1, further comprising:

a bending sensor configured to measure a curvature of the eyeball and generate a curvature information of the eyeball, wherein the image processing device generates the image of the internal structure of the eyeball by adjusting interference of the echo signal received by each of the plurality of transducers based on the curvature information of the eyeball.

3. The intraocular pressure measurement system of claim 1, wherein the image processing device measures the intraocular pressure of the internal structure of the eyeball based on a relationship between velocity of a shear wave induced by the first ultrasound signal within the eyeball and stiffness of the internal structure of the eyeball.

4. The intraocular pressure measurement system of claim 1, wherein the probe, the ultrasound transmitter, and the ultrasound receiver are attached to a periphery of the eyeball or directly attached to the eyeball, and wherein the image processing device is included in a mobile device.

* * * * *